United States Patent [19]

Hölter et al.

[11] Patent Number: 4,742,763
[45] Date of Patent: May 10, 1988

[54] DEVICE FOR THE DETECTION OF NOXIOUS SUBSTANCES IN THE AIR SUPPLIED TO A COMPARTMENT OCCUPIED BY PEOPLE

[75] Inventors: Heinz Hölter; Heinrich Igelbüscher, both of Gladbeck; Heinrich Gresch, Dortmund-Wickede; Heribert Dewert, Gladbeck, all of Fed. Rep. of Germany

[73] Assignee: Heinz Holter, Gladbeck, Fed. Rep. of Germany

[21] Appl. No.: 2,712

[22] PCT Filed: Apr. 19, 1986

[86] PCT No.: PCT/EP86/00239
§ 371 Date: Dec. 10, 1986
§ 102(e) Date: Dec. 10, 1986

[87] PCT Pub. No.: WO86/06331
PCT Pub. Date: Nov. 6, 1986

[30] Foreign Application Priority Data

Apr. 23, 1985 [DE] Fed. Rep. of Germany ....... 3514588
May 22, 1985 [DE] Fed. Rep. of Germany ....... 3518320
Jun. 26, 1985 [DE] Fed. Rep. of Germany ....... 3522834

[51] Int. Cl.$^4$ ............................................. B60H 3/06
[52] U.S. Cl. ...................... 98/2.01; 98/2.11; 422/83
[58] Field of Search ............... 98/2.01, 2.11; 422/83

[56] References Cited

U.S. PATENT DOCUMENTS 2,899,282 8/1959 Eyraud .
3,088,809 5/1963 Boatman ................... 422/83 X
4,170,455 10/1979 Henrie ..................... 422/83 X
4,581,988 4/1986 Mattei ................... 98/2.01 X
4,610,703 9/1986 Kowalczyk ................... 98/2.11

FOREIGN PATENT DOCUMENTS 0042287 12/1981 European Pat. Off. .
0157247 10/1985 European Pat. Off. .
0157237 10/1985 European Pat. Off. .
3100681 8/1982 Fed. Rep. of Germany .
3304324 8/1984 Fed. Rep. of Germany .
85/01704 4/1985 PCT Int'l Appl. .

Primary Examiner—Harold Joyce
Attorney, Agent, or Firm—Karl F. Ross; Herbert Dubno; Ronald Lianides

[57] ABSTRACT

One or more sensors are used for the indication and/or control and/or adjustment of filter devices and/or ventilation systems in relation with a measured value or respective measured values, established by the sensor, or respective sensors. In order to provide an economically simple and maintainance free device of the aforementioned kind with reduced space requirements, which responds to all common air pollutants and insures a reliable reading, the invention proposes that the sensor be placed in a housing with a side facing the oncoming flow preceded within the housing by a measuring slot abutting an air chamber of the housing, where a pulsator is located, whereby one or more air-inlet openings lead to the cylinder space of the air chamber facing away from the sensor. The pulsator consists of a piston coupled with an oscillator. In the air chamber an air-conditioning device, preferably a heating device, is provided.

18 Claims, 1 Drawing Sheet

DEVICE FOR THE DETECTION OF NOXIOUS SUBSTANCES IN THE AIR SUPPLIED TO A COMPARTMENT OCCUPIED BY PEOPLE

FIELD OF THE INVENTION

The invention relates to a device for the detection of noxious substances in the air supplied to a compartment to be occupied by people, preferably the cab of a motor vehicle, by using one or several sensors and for the indication and/or control and/or adjustment of filter arrangements and/or ventilation systems in relation to the measured value, are respective measured values, detected by a sensor, or respective sensors.

BACKGROUND OF THE INVENTION

In order to eliminate the noxious substances contained in the air supplied to a compartment occupied by people, it is first necessary to detect them and then to produce signals or control outputs in order to switch on or off—the filtering systems and/or the ventilation systems.

It has already been proposed to provide analyzers, which however are comparatively expensive to acquire and to operate, not to mention that they are capable of detecting only separate components of noxious substances.

Further, it is known to use semiconductor sensors for these purposes, which meet the general requirement to respond to the usual air pollutants. However, the range of responsiveness of these sensors lies well above the objectionable level of concentration of many noxious substances to which people are subjected. Besides, semiconductor sensors are sensitive to temperature fluctuations and differences in flow velocity of the air streams to be analyzed. Furthermore, the response time of these sensors, particularly in the case of low concentrations, and their decontamination time are too high for their use for instance for the control of filter systems and/or ventilation systems in motor-vehicle cabs.

OBJECT OF THE INVENTION

Departing from this state of the art, the invention has the object to provide an economical and maintenance-free installation with low space requirements, avoiding the aforementioned disadvantages, which responds to all the usually occurring air pollutants and insures a dependable reading.

SUMMARY OF THE INVENTION

In accordance with the invention, this object is attained due to the fact that the sensor is placed in a housing and within this housing, in front of its side exposed to the oncoming stream, a measuring slot for the passage of the air streams to be surveyed is provided, leading to an air chamber of the housing wherein a pulsator is mounted, whereby one or several air-inlet openings abut in the cylindrical area of the air chamber facing away from the sensor. Due to this configuration, it is possible to feed the sensor only a predetermined amount of air, so that the sensor can furnish the desired reading, independently from the variations in the flow velocity. The used oscillatory pump system insures a constant air flushing of the sensor and leads to the shortening of the decontamination time.

Advantageously, one or several air-outlet openings lead from the cylinder area of the air chamber facing the sensor, so that an extensively uniformized and constant air flow hits the sensor.

In the area downstream of the sensor, air-outlet channels are provided in a wall of the housing, through which that portion of the air entered the housing, which effected the impact on the sensor, can exit.

The pulsator consists of a piston coupled with an oscillator, whereby the oscillator preferably constitutes the final portion of the housing facing away from the sensor, so that altogether a very compact construction unit results.

According to a further feature of the invention, in different flow directions, the piston presents different flow resistances. When the piston is set to oscillate, it produces a directed air flow which is aimed at the sensor through the measuring slot. For this purpose, the piston is provided on its outside with a saw-tooth-shaped profile, so that the widened portions are aligned in the direction of the sensor. Through the piston oscillations a predetermined air flow is created, whereby at the same time the absorption into the housing of the air to be surveyed is effected.

The air-inlet and air-outlet openings are asymmetrical in their passage cross-sections. These for instance widen starting from the air chamber towards the outside, like a diffuser. This way it is insured that, during the air pulsations caused by the oscillator, sufficient air enters the housing to create an abundant flushing of the sensor.

Preferably, in the air chamber an air-conditioner, for instance an air heater, is provided. This is located in the air chamber in the area between the pulsator and the measuring slot. Through this conditioning a uniform tempering of the air amounts directed towards the sensor is provided, so that it is impacted upon when in its optimal response range. Thus, the sensor delivers a signal which is not dependent on temperatures, to the widest possible extent. This way, the characteristic curve of the sensor is so traced in its lower operational range, that readings for noxious substances can be performed even in the low-concentration range.

According to a further feature of the invention, a heating device is assigned to the pulsator. This is preferably located in the wall of the housing and/or in the area between the housing wall and the pulsator and/or on the outside of the pulsator. Due to this additional heating device, for instance an electrical heating wire, an additional heating of the air mass to be surveyed is achieved already in the area of the oscillating piston, which proves to be particularly advantageous for the winter months.

According to a further feature of the invention, the sensor is located in a pressure-proof housing, wherein a preconditioned air mass is supplied to the sensor in a compressed state, so that even slight traces of noxious substances are technically measurable by the sensor and can serve to produce a reading and/or an adjusting impulse.

According to another feature of the invention, the air column in front of the side of the sensor facing the oncoming flow is made to vibrate, namely in high-frequency vibrations. The vibrating air column acting upon the side of the sensor facing the oncoming flow leads to a comparatively very rapid "flushing" of the foreign substances deposited on the side of the sensor facing the oncoming flow, and thereby to a considerable decrease of the decontamination time, whereby possible influences stemming from the externally impacting flow are precluded due to the outer housing.

Within the framework of the invention, it is also possible to heat the side of the sensor exposed to the oncoming flow, in order to achieve the most constant temperature conditions possible.

BRIEF DESCRIPTION OF THE DRAWINGS

An embodiment of the invention is described with the aid of the drawing, in which.

SPECIFIC DESCRIPTION

Figure 1:
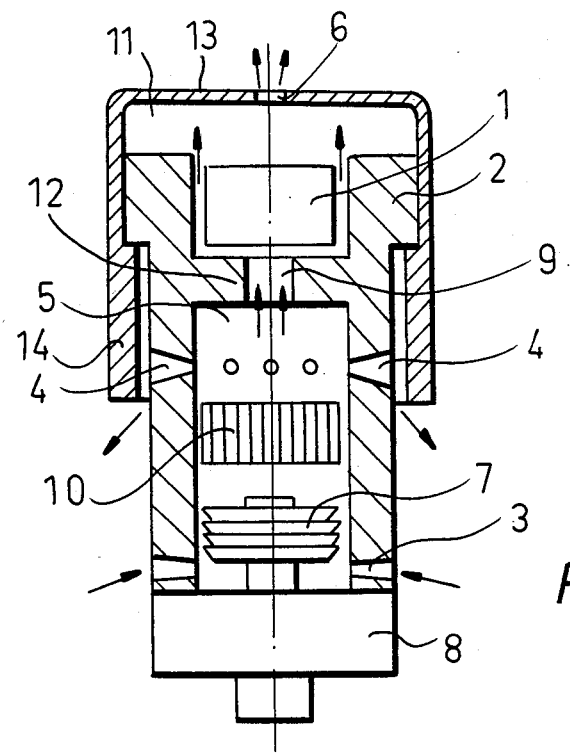
FIG. 1 is an axial sectional view of the device.

The sensor is located in an air chamber 11 formed in a housing 2 in front of a measuring slot 9 formed in the wall 12 facing the oncoming flow of air within the housing 2. The measuring slot 9 leads to the cylindrical air chamber 5 of the housing 2. In this air chamber 5, a pulsator 7 is arranged. The air-inlet openings 3 are formed in the cylinder area of the air chamber 5 upstream from pulsator 7. The air-outlet openings 4 lead away from the cylinder area of the air chamber 5 downstream from the pulsator 7. In the area downstream of the sensor 1, in the up side of the housing wall is an air-outlet channel 6.

The pulsator 7 forms a piston coupled with an oscillator 8. The oscillator 8 constitutes the final portion of the housing remote from the sensor 1. Preferably the oscillator 1 is a magnet free oscillator.

The upper or outlet end of the housing 2 is provided with a cap 13, which defines with the housing 2 the air chamber 11, the cap 13 having a skirt 14 spaced from the housing body and extending downwardly to overlie the openings 4 for preventing air from the airstream being tested from entering the openings 4.

Figure 2:
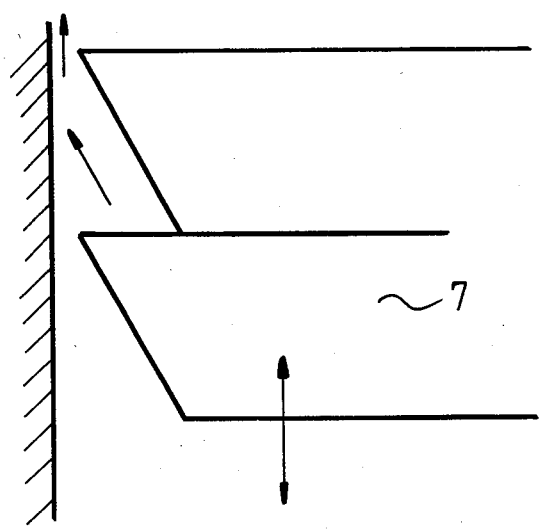
FIG. 2 is a larger scale detail of FIG. 1, illustrating the pulsator.

As can be seen especially from FIG. 2, the piston serving as the pulsator 7 is provided on its outside with a saw-tooth-like profile, whereby the widened areas are aligned in the axial direction of the sensor 1. In FIG. 2, the oscillation direction of the pulsator 7 is indicated with the double arrow and the air flow directed towards the sensor 1 is marked with multiple arrows.

The air-inlet openings 3 and the air-outlet openings 4 widen from the air chamber 5 towards the outside like diffusers.

In the air chamber 5 an air-conditioning device 10 is provided, which is located in the area between the pulsator 7 and the measuring slot 9. For the sake of a more general view, it has not been further illustrated that the pulsator 7 can have a heating device, for instance an electrical heater coil, which can be located in the neighboring wall of the housing 2, between the walling of the housing and the pulsator 7 but also on the outside of the pulsator, in the area of the saw-tooth-like profile.

We claim:

1. A device for the detection of noxious substances in air being supplied to a compartment occupied by people, said detection device comprising:

a housing centered on an upright axis and adapted to be traversed by an air flow to be analyzed;

a first air chamber formed in said housing;

a second air chamber formed in said housing upstream of said first chamber, said second chamber being cylindrical and centered on said axis;

a sensor disposed in said first chamber;

a measuring slot formed in a wall of said housing separating said first and second chambers, said measuring slot being upstream of said sensor and in registration therewith for directing said air flow against said sensor;

a pulsator disposed in said second chamber for controlling said air flow through said housing to insure a constant air flushing of said sensor;

at least one air inlet formed in said housing and opening into said second chamber upstream of said pulsator for the admission of air into said second chamber; and at least one first air outlet formed in said housing at one end thereof and opening into said first chamber downstream of said sensor for venting said air flow from said first chamber.

2. The detection device defined in claim 1 further comprising at least one second air outlet formed in said housing and opening into said second chamber downstream of said pulsator for venting a portion of said air flow from said second chamber to provide a uniform and constant air flow to said sensor.

3. The detection device defined in claim 1 further comprising an oscillator coupled with said pulsator, said pulsator forming a piston driven by said oscillator for producing an air flow directed at said measuring slot.

4. The detection device defined in claim 3 wherein said oscillator forms another end of said housing opposite from said one end.

5. The detection device defined in claim 3 wherein said piston has different flow resistances in different flow directions.

6. The detection device defined in claim 3 wherein said piston is circular and centered on said upright axis, said piston having a saw tooth outline with peaks thereof lying in alignment in the axial direction.

7. The detection device defined in claim 2 wherein said air inlet and second air outlet are noncylindrical.

8. The detection device defined in claim 7 wherein said air inlet and said second air outlet widen outwardly to form respective diffusers.

9. The detection device defined in claim 1 further comprising an air conditioning device disposed in said second chamber between said pulsator and said measuring slot.

10. The detection device defined in claim 9 wherein said air conditioning device is a heating device.

11. The detection device defined in claim 1 further comprising a heating device for said pulsator.

12. The detection device defined in claim 11 wherein said heating device for said pulsator is disposed in a wall of said housing adjacent said pulsator.

13. The detection device defined in claim 11 wherein said heating device for said pulsator is disposed between a wall of said housing and said pulsator.

14. The detection device defined in claim 11 wherein said heating device for said pulsator is disposed on said pulsator.

15. The detection device defined in claim 9 wherein said housing is pressure-proof, whereby a preconditioned quantity of air can be fed to said sensor in a compressed state.

16. The detection device defined in claim 3 wherein said air flow forms a column which is caused to vibrate by said piston driven by said oscillator, preferably at a high frequency, in front of the side of said sensor against which said air flow is directed.

17. The detection device defined in claim 1 wherein the side of said sensor against which said air flow is directed is heated.

18. The detection device defined in claim 2 further comprising a skirt provided on said housing overlying said second air outlet and spaced therefrom for preventing air from an airstream being tested from entering said second air outlet.

* * * * *